United States Patent [19]

LeMay

[11] 4,038,551

[45] July 26, 1977

[54] CIRCUIT FOR PROCESSING SIGNAL DATA OBTAINED FROM AN AXIAL TOMOGRAPHIC SCANNING APPARATUS

[75] Inventor: Christopher Archibald Gordon LeMay, Osterley, England

[73] Assignee: E M I Limited, Haynes, England

[21] Appl. No.: 609,718

[22] Filed: Sept. 2, 1975

Related U.S. Application Data

[62] Division of Ser. No. 462,104, April 18, 1974, Pat. No. 3,924,129.

[30] Foreign Application Priority Data

| Apr. 25, 1973 | United Kingdom | 19528/73 |
| Aug. 21, 1973 | United Kingdom | 39420/73 |
| Oct. 11, 1973 | United Kingdom | 47507/73 |

[51] Int. Cl.² ............................................. G01N 21/34
[52] U.S. Cl. .................................................. 250/445 T
[58] Field of Search ............... 250/362, 363, 366, 369, 250/336, 395, 445 T

[56] References Cited

U.S. PATENT DOCUMENTS 3,778,614  12/1973  Hounsfield ..................... 250/445 T Primary Examiner—Davis L. Willis
Attorney, Agent, or Firm—Fleit & Jacobson

[57] ABSTRACT

A circuit is disclosed for operating upon output signals indicative of the absorption suffered by penetrating radiation on traversing respective beam paths through a substantially planar section of a body under examination to effect a form of convolution of said signals as described in U.S. Pat. No. 3,924,124. The output signals are applied in time sequence to the circuit and each signal is arranged to traverse the circuit and return to the input thereof in time to be added to the next signal in the sequence. In traversing the circuit, however, a signal is multiplied by a factor less than unity; thus the component of a signal circulating in the circuit, as added to successive signals in the sequence, is progressively reduced.

8 Claims, 11 Drawing Figures

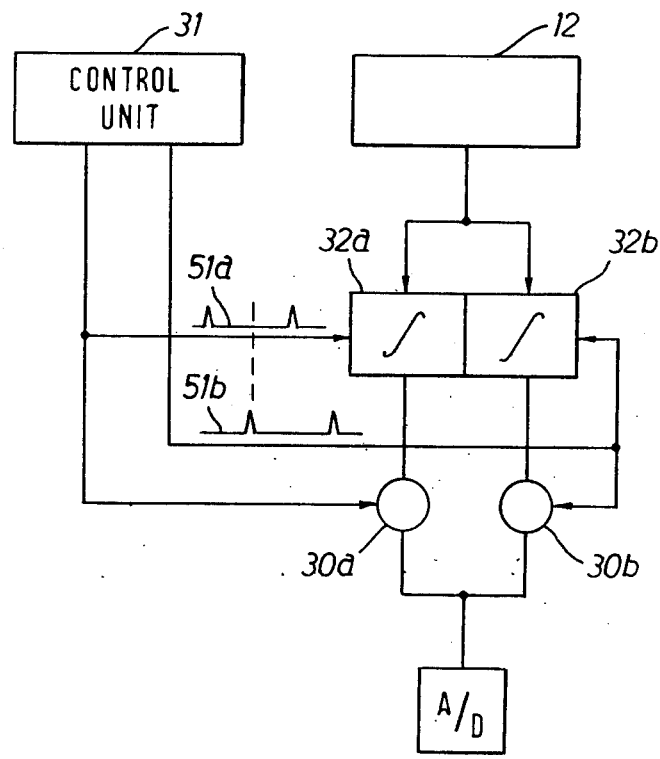
FIG. 3
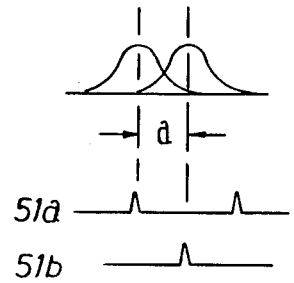

FACTORS FOR $\beta = 0.625$, SINGLE BEAMS $L_0 = 1.0000$
$L_1 = -0.44447$
$L_2 = -0.01498$
$L_3 = -0.02548$
$L_4 = -0.002699$
$L_5 = -0.006653$
$L_6 = -0.004478$
$L_7 = -0.003331$
$L_8 = -0.002552$
$L_9 = -0.002022$
$L_{10} = -0.001639$
$L_{11} = -0.001356$
$L_{12} = -0.001140$
$L_{13} = -0.0009717$
$L_{14} = -0.0008381$
$L_{15} = -0.0007306$
$L_{16} = -0.0006422$
$L_{17} = -0.0005692$
$L_{18} = -0.0005073$
$L_{19} = -0.0004559$
$L_{20} = -0.0004114$

*FIG. 7*

CIRCUIT FOR PROCESSING SIGNAL DATA OBTAINED FROM AN AXIAL TOMOGRAPHIC SCANNING APPARATUS

This is a divisional of U.S. Ser. No. 462,104 filed Apr. 18, 1974 now U.S. Pat. No. 3,924,129.

This invention relates to a method of and apparatus for constructing a representation of the variation of absorption of a planar slice of body with respect to penetrating radiation such as X or γ radiation.

The method and apparatus according to the invention can be used to assist in the production of radiographs in any convenient form, such as a picture on a cathode ray tube or other image forming device, a photograph of such a picture, or a map of absorption coefficients such as may be produced by a digital computer and on which contours may subsequently be drawn.

One method of, and apparatus for, constructing a representation of the variation of absorption of a planar slice of a body with respect to penetrating radiation is described in U.S. Pat. No. 3,778,614. According to this specification, radiation is directed through part of the body, from an external source, in the form of a pencil beam. A scanning movement is imposed on the beam so that it takes up in turn a large number of differing dispositions, and a detector is used to provide a measure of the absorption of the beam in each such disposition after the beam has passed through the body. So that the beam takes up these various dispositions the source and the detector are reciprocated in a plane and are orbited about an axis normal to the plane. The various dispositions thus lie in a plane through the body over which the distribution of absorption coefficient for the radiation used in derived by processing the beam absorption data provided by the detector. The processing is such that the finally displayed distribution of absorption is the result of a linear superimposition process coupled with successive approximations.

The method and apparatus described in the aforesaid United States Patent has proved to be successful for producing cross-sectional representation of parts of the living body, such as the head.

It is one object of this invention to provide an improved method of and apparatus for constructing a representation of the variation of absorption of a planar slice of a body with respect to penetrating radiation such as X or γ radiation which utilises a novel and advantageous technique of processing beam absorption data.

In a paper by G. N. Ramachanadran and A. V. Lakshminarayanan entitled "Three-dimensional reconstruction from Radiographs and Electron micrographs: Application of Convolutions instead of Fourier Transforms," and published in The Proceedings of the National Academy of Sciences, U.S.A., Vol. 68, No. 9 page 2236, September 1971, there is described a mathematical procedure which in principle is applicable to the reconstruction of cross sectional representations from absorption data such as that obtained from apparatus described in the aforesaid United States Patent. However the procedure, when reduced to practical application as described in the paper, does not yield accuracy and resolution to the degree required for examination of most parts of the human body.

It is another object of this invention to provide an improved method and apparatus for constructing a representation of the variation of absorption of a planar slice of a body with respect to penetrating radiation such as X or γ radiation which utilises signal processing based on a principle which bears a relationship to convolution and is capable of giving a high degree of accuracy and resolution.

It is another object of the present invention to provide an improved method of and apparatus for constructing a representation of the variation of absorption of a planar slice of a body with respect to penetrating radiation such as X or γ radiation with a view to achieving rapid yet accurate signal processing.

It is yet another object of the present invention to provide an improved method of and apparatus for constructing a representation of the variation of absorption of a planar slice of a body with respect to penetrating radiation, such as X or γ radiation, in which a desired degree of aperture correction can be introduced simply without the addition of special apparatus.

It is yet another object of the present invention to provide an improved method of and apparatus for constructing a representation of the variation of absorption of a planar slice of a body with respect to penetrating radiation, in which a representation of a cross sectional slice of the body can be produced with high accuracy and resolution with the aid of many beams, but in which nevertheless the amount of signal processing and equipment required therefor is relatively small.

A still further object of the invention is to provide an improved method of and apparatus for constructing a representation of the variation of absorption of planar slice of a body with respect to penetrating radiation such as X or γ radiation in which the processing of signals for many beams is carried out in overlapping time sequence in the same recirculating system.

In accordance with one aspect of the present invention there is provided a method of constructing a representation of the variation of absorption of a planar slice of a body with respect to penetrating radiation which comprises the steps of:

a. providing a plurality of sets of $m$ beam data signals where $m$ is of the order of 50 or greater, the signals of each set representing or being related to the logarithm of the absorption of a corresponding set of substantially parallel beams of said radiation in the plane of said slice, and the sets of signals corresponding effectively to sets of parallel beams, orientated at different angles in said plane, b. providing a series of factor signals of which the number of terms is of the order of the number $m$ of effective beams per parallel set, said factor signals at least after the factor signal of order 5 conforming to a substantially monotonic function, c. deriving for a particular beam data signal a summation signal by forming the sum of said beam data signal multiplied by the zero order factor signal, the next adjacent beam data signals of the same set multiplied by the first order factor signal, the second adjacent beam data signals of the same set multiplied by the second order factor signal and so on over a desired range, d. deriving for other beam data signals, some in every set, respective summation signals by repeating method step (c) in respect of each said other beam data signals, e. forming the sum of summation signals corresponding to beams of different sets intersecting a particular elementary area of the planar slice to produce a signal representing the absorption of said elementary area, f. repeating method step (e) in respect of other elementary areas of said planar slice, thereby to construct said representation, g. said substantially monotonic function being such that the signal representing the absorption of any elementary areas is successively more accurately compensated for absorption suffered outside the respective elementary area by the beams intersecting the respective elementary area, as successively higher order factor signals (multiplied by respective beam data signals) are utilized in the formation of said summation signals.

In accordance with another aspect of the invention there is provided apparatus for constructing a representation of the variation of absorption of a planar slice of a body with respect to penetrating radiation which comprises:

a. a source of a plurality of sets of $m$ beam data signals $m$ is of the order of 50 or greater, the signals of each set representing the logarithm of the absorption of a corresponding set of substantially parallel beams of said radiation in the plane of said slice, and the sets of signals corresponding effectively to sets of parallel beams, orientated at different angles in said plane, b. a source of a series of factor signals of which the number of terms is of the order of the number $m$ of effective beams per parallel set, said factor signals at least after the factor signal of order 5 conforming to a substantially monotonic function, c. derivation means for deriving respective summation signals for a plurality of beam data signals, some in every set, said derivation means including means for forming, for each of said plurality of beam data signals, the sum of the respective beam data signal multiplied by the zero order factor signal, the next adjacent beam data signals of the same set multiplied by the first order factor signal, the second adjacent beam data signals of the same set multiplied by the second order factor signal and so on over a desired range, thereby to derive the summation signal for each of said plurality of beam data signals, d. and means for forming the sum of summation signals corresponding to beams of different sets intersecting each of a plurality of elementary areas of the planar slice to produce signals representing the absorption of said elementary area, thereby to construct said representation, e. said substantially monotonic function being such that the signal representing the absorption of any elementary area is successively more accurately compensated for absorption suffered outside the respective elementary area by the beams intersecting the respective elementary area, as successively higher order factor signals (multiplied by respective beam data signals) are utilized in the formation of said summation signals.

Other features of the invention comprise a method of and means for producing manipulation of signals in accordance with a convolution principle and for producing the effect of aperture correction.

In order that the invention may be more fully understood and readily carried into effect, it will now be described by way of examples with reference to the accompanying drawings in which:

FIG. 1 illustrates diagrammatically the scanning mechanism of apparatus for examining a body by means of X radiation in accordance with one example of the present invention, FIG. 2 is a diagrammatic representation of the circuit for processing the signals derived from the scanning mechanism to convert them into signals representing the logarithmic absorption suffered by an exploring beam traversing many sets of parallel paths, FIG. 3 is a more detailed block diagram of part of FIG. 2, FIG. 4 is a diagrammatic representation of a circuit for reconstructing images utilising the signals output from the circuit of FIG. 2;

FIG. 7 is a list of factors which are utilised in the circuit represented in FIG. 3;

Figure 1:
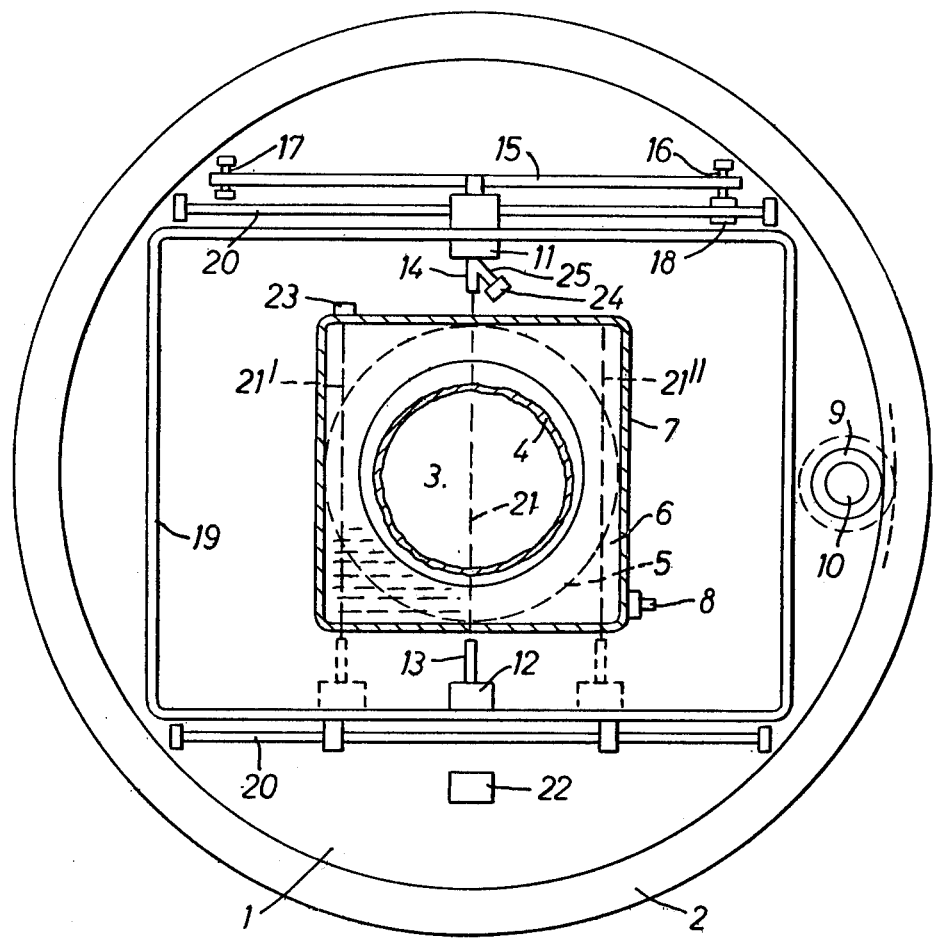

Referring to the drawings, the apparatus which is in a form adapted to examination of the head of the patient comprises a rotary member 1 which is rotatable inside a fixed casing 2 forming part of the main frame of the apparatus. The rotary member 1 has a central aperture 3 in which the head of the patient to be examined can be inserted. The central aperture is closed in a water-tight manner by a pouched cover 4 of flexible material which is secured to a sealing flange 5. This flange is held in sealing, but rotatable, relationship with the remote face of the member 1. The pouch is shown in section in FIG. 1. The head of the patient is inserted through the aperture 3 into the pouch of the cover 4, and an additional head rest, not shown, may be provided to support the head in the pouch. A suitable chain or bed is provided to support the patient during the examination. When the head is inserted through the aperture 3 into the pouch 4 it projects into a water reservoir 6 having side walls 7, the pouch separating the head from the water. The reservoir is closed at the front by the member 1 and cover 4, at the side by the walls 7 which are made of plastic, and at the rear by a base wall, not shown. The walls 7 and the base wall rotate with the member 1, whereas the cover 4 with its flange 5 remains stationary, the flange being secured to the frame of the apparatus. A pipe 8 is connected to a pump for feeding water to and from the reservoir and after the patient's head has been inserted in the pouch, water is pumped into the reservoir 6 so as to expel the air from between the pouch and the patient's head.

A toothed-gear wheel 9, driven by a motor 10 is provided for driving the rotatable member 1 so as to produce orbital scanning of the member 1 about its axis, which is also the axis of the aperture 3. The gearwheel 9 engages teeth formed around the inner periphery of the casing member 2. The rotatable member carries a source 11 of penetrating radiation, an X-ray generating tube in this example, and facing the source 11, on the other side of the aperture 3 there is provided an X-ray detector 12. The detector 12, which comprises a scintillating crystal and a photomultiplier, has a collimator 13. The source of the radiation 11 is arranged to be an effective point source and it has a collimator 14, the collimators 13 and 14 confining the radiation reaching the detector 12 to a single narrow beam 21 lying in a plane section normal to the axis of the rotary member 1. The plane lies within the reservoir 6.

The source 11 is secured to a toothed belt 15 driven by a toothed drive shaft 16 journalled in the rotatable member 1, the belt being extended between the shaft 16 and the second shaft 17 also journalled in the member 1. The shaft 16 is driven by a reversible motor 18, the controls of which are interlocked with those of the motor 10. Since the source 11 is massive, a counter balance weight, not shown, is provided secured to the other run of the belt so as to move reciprocally with the source. In operation of the apparatus, the source 11 and the collimator 14 are caused by the motor 18 to execute to and fro lateral scanning movements in the aforementioned plane normal to the axis of the rotary member 1. The detector 12 with its collimator 13 are coupled to the source 11 by a yoke 19 so that they execute the same lateral scanning movements. Guides 20 are provided to support the source and the yoke during the lateral scanning. Output signals are derived from the detector 12 during each lateral scan and these signals represent the transmission or absorption of the beam 21 along a sampling set of closely spaced parallel beam paths in the planar section under examination.

The interlock between the motors 10 and 18 is such that following each lateral scan, in one or other direction, an increment of orbital movement of say 1° is imparted to the rotary member 1 by the motor 10. Thereafter another lateral scan occurs under the control of the motor 18 but this time in the reverse direction to the preceding lateral scan. A further set of output signals representing the transmission of the beam 21 along a further set of closely spaced parallel beam paths is derived, this set of beam paths being orientated at 1° relative to the preceding set. A photocell device, represented diagrammatically by the block 22, and co-operating with the graticule, not shown, coupled to the yoke 19, is provided to monitor the lateral scanning displacements and determine the timing of the output signals. The alternate orbital and lateral scanning movements are continued until a total orbital movement of 180° has been completed.

As indicated in FIG. 1, the reservoir 6 has a lateral extent substantially equal to that of the lateral scan, the extremities of which are indicated by the dotted beams 21' and 21". It projects to either side of the aperture 3 so that at the beginning of each lateral scan the beam 21 is for a time traversing a known path length through the water in the reservoir. The reservoir, when filled with water, thus provides a reference attenuator so positioned relative to said locating means as to provide a known attenuation of the beam 21 at the beginning of each lateral scan before the beam passes to the body to be examined. As will appear subsequently a reference signal is derived from the detecting means while the beam is intercepted by the water reservoir and this reference signal is utilised for modifying output signals derived when the beam is intercepted by the body to be examined. As the walls of the reservoir, other than the cover 4, rotate with the member 1, the path of the beam through the reference attenuator provided by the side portions of the reservoir 6 is substantially the same for every lateral scan regardless of the angular orientation. There is also provided mounted on the member 1 a block of lead 23 which is located at one extremity of the lateral scans carried out by the source 11 and detector 12. The lead block 23 provides substantially complete absorption of the X-radiation and the output signal from the detector 12 when the beam is intercepted by the lead provides a second reference signal which is utilised to modify the signals derived from the detector not only when the beam 21 is intercepted by the body to be examined, but also when it is intercepted by the parts of the reservoir which act as reference attenuators. It is to be noted that the reservoir 6 provides attenuation of the beam 21 throughout the lateral scanning movements, but the attenuation is reduced in the regions where the beam is liable to be intercepted by the body to be examined. The attenuation or asborption coefficient of water is such that the total absorption of the beam 21 is approximately the same throughout each lateral scan, when the body to be examined is positioned in the pouch (except of course when the beam is intercepted by the lead block 23). In the circuit for processing the output signals of the detector 12 the logarithm of the reference signal derived when the beam suffers the known attenuation at the beginning of each lateral scan is subtracted from the logarithm of the other output signals, and the resultant output signals represent substantially only differences in the attenuation of the beam within the body examined from that of transmission through water.

A reference detector 24 is mounted close to the X-ray source 11 so that it receives radiation directly from the source via a collimator 25. The detector 22 is provided to monitor the energy of the X-rays.

The circuit of the apparatus set out in FIG. 2 commences with the detectors 12 and 24 of the mechanism that has been described with reference to FIG. 1. The output signals of the detector 12 are applied to a gate 30 which is opened at predetermined times by sampling pulses from a master control circuit 31. This master control circuit receives input signals from the photocell device 22 and feeds out suitable control signals not only to the gate 30 but also to the motor 10 and to the reversing motor 18. The sampling pulses which it feeds to the gate 30 are produced at times determined by the aforesaid graticule so as to derive from the detector 12 a succession of output signals corresponding to the transmission of the beam 21 through a sampling set of parallel beam paths, as already indicated. The orientation for the set of paths is determined by the angular position or the rotatable member 1. During each sampling interval the output of the detector 12 is integrated in an integrator 32 and then converted to digital code form in an analogue-to-digital converter 33. The signal generated during each sampling pulse is stored in its digital form in a store 34. The X-ray beam 21 is intercepted by the lead block 23 once in two lateral scans and therefoe the corresponding output signal from the detector 12 is stored for the duration of two traverses. The signals of a particular parallel set of paths in the store 34 include those obtained when the X-ray beam 21 is known to pass through the reference paths in the reservoir 6 and those obtained when passing through the body under examination. Gate 35 is provided for selecting the output signal derived from the detector at the time when the beam 21 is substantially interrupted by the lead block 23. Another gate 36 is provided for selecting the signals derived at other traversal times. The selection is controlled by sampling pulses derived from the master control circuit 31 in such a way that the reference signal representing the virtually complete attenuation introduced by the load is subtracted from each other signal of a sampling set, so that after the subtraction the resulting signals represent the transmission or absorption of the beam 21 within the examined body related to the absorption of lead as a datum. In this way the effect of 'after glow' in the detector 12 is largely removed. The resulting signals are passed into dividing circuit 38.

The reference detector 24 previously referred to has an output gate 40 which receives sampling pulses from the master control circuit 31, coincident with the sampling pulses applied to the gate 30. Signals passing through the gate 40 are integrated in an integrator 41 and converted to digital form in a converter 42, these components 41 and 42 corresponding to the integrator 32 and converter 33. The digitised signals from the detector 24 are then passed to a store 43 and applied thence to the aforesaid dividing circuit 38.

In the dividing circuit each signal from the detector 12 is divided by the corresponding signal from the store 43 to compensate for variations in energy of the source 11. The signals so compensated are passed to a log converting circuit 45 which translates each signal from the detector 12, referenced on lead as the datum as explained, into its logarithm and holds them in this form. These signals are applied to two gates 46 and 47 which are controlled by pulses from the master control circuit 31. The gate 46 is opened at times corresponding to those when the X-ray beam 21, during any particular traverse, is passing through the region in which the body to be examined may be located, while the gate 47 is opened at other times corresponding to when the beam 21 is passing through the reference paths in the water and is therefore subjected to a known attenuation. The signals from the gate 47 may therefore be termed reference signals, those from the gate 46 being distinguished as output signals. The reference signal moreover is read out repeatedly to coincide with each output signal of a particular scan, and it is subtracted from these output signals so that the output signals then represent the ratio of the attenuation of the beam 21 to the known attenuation produced by the water in the reservoir. Any spurious variations in the output signals, due to rapid drift of the sensitivity of the detector 12 are thus substantially compensated. The output signals after these modifications are fed to the signal processor 50 to participate along with the output signals of all the other sets in the image reconstruction of the distribution of absorption of the exploring radiation in the section of the body under examination.

Figure 2:
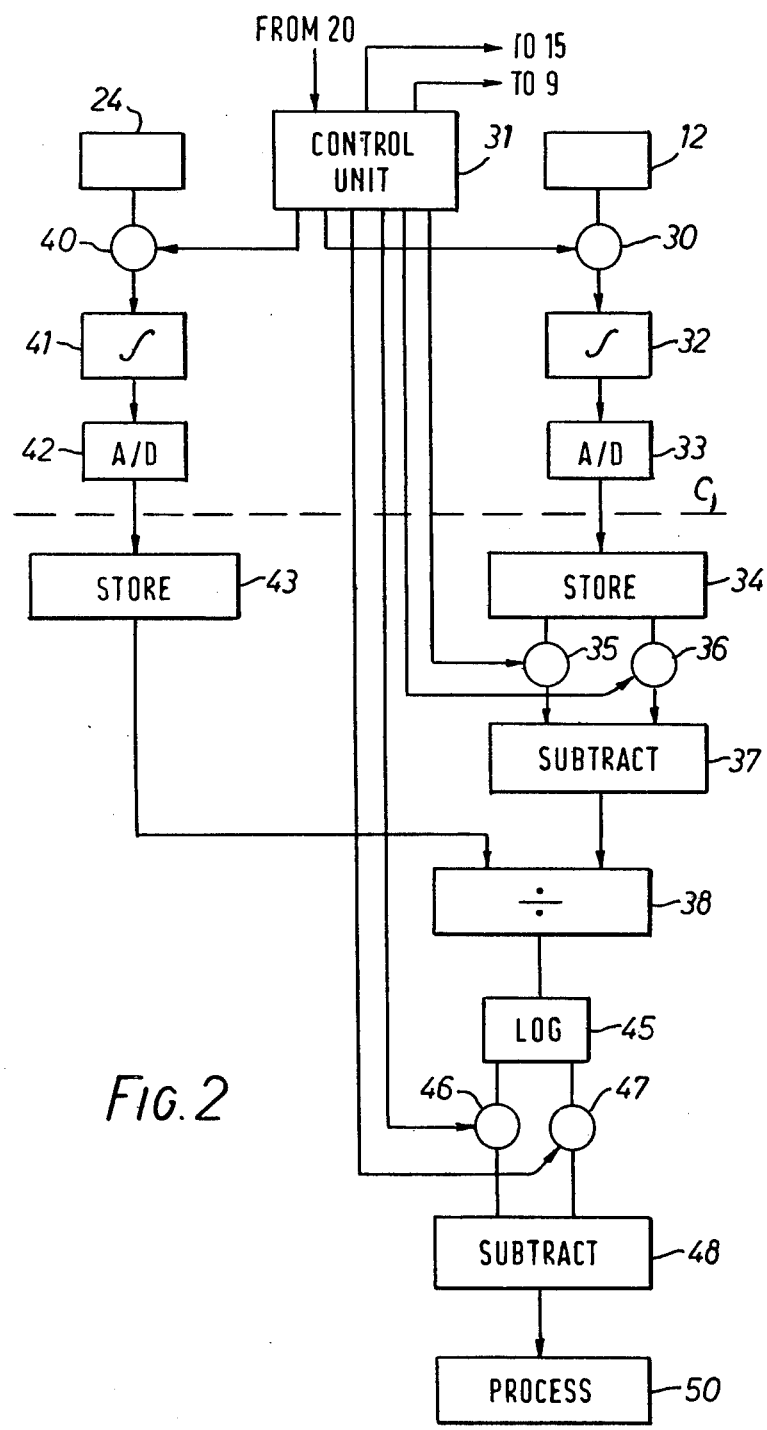

As shown in FIG. 3, the gate and integrator circuit 30, 32 illustrated generally in FIG. 2 consists in the example described of two integrators 32a, 32b and two gates 30a, 30b. The integrators, which are Miller integrators of known construction, are connected to receive continuous inputs for the detector 12, and to integrate these inputs. However, the integrator 32a receives short duration pulses 51a at regular intervals during which intervals the source 11 and detector 12 move a distance 2a. The integrator 32b receives similar short duration pulses 51b, but the latter pulses are interleaved with those applied to the integrator 32a. The pulses initiate read and reset operations in the two integrators, these operations occupying a time interval which is negligibly short compared with the time interval between adjacent pulses. The pulses fed to the integrators are also applied to the gates 30a and 30b respectively to couple the respective integrators to the analogue-to-digital converter 33, during the reading process. This mode of operation coupled with appropriate dimensioning of the collimators 13 and 14 has the effect of causing each signal, converted to digital form by the converter 33, to represent the transmission of a virtual beam of width at least 2a, and having an approximately sinusoidal distribution of intensity across its width, as depicted by the graph adjacent the output lead of the converter 33. The collimators 13 and 14 are rectangular in cross section, but because of the nature of the source of the radiation and of the radiation itself the "virtual" beam intensity distribution falls away smoothly from its central maximum. Moreover, as indicated by the graph, the output signal from the converter 33 represents the absorption sampling in the examined cross section by parallel beams spaced by a sampling interval of $a$. The gate and integrator circuit 40, 41 of FIG. 2 is of the similar construction as that shown in FIG. 3. In the present example of the invention, the integrators 32a and 32b are controlled to provide 160 or more beam data signals in each lateral scanning movement while there are 180 such sets of signals. The number of beam data signals per set and the number of sets may of course vary, but is always sufficiently large to provide an image of high definition. In practice each number will be of the order of 50 or more to allow for the reconstruction of images of varying sizes.

Figure 4:
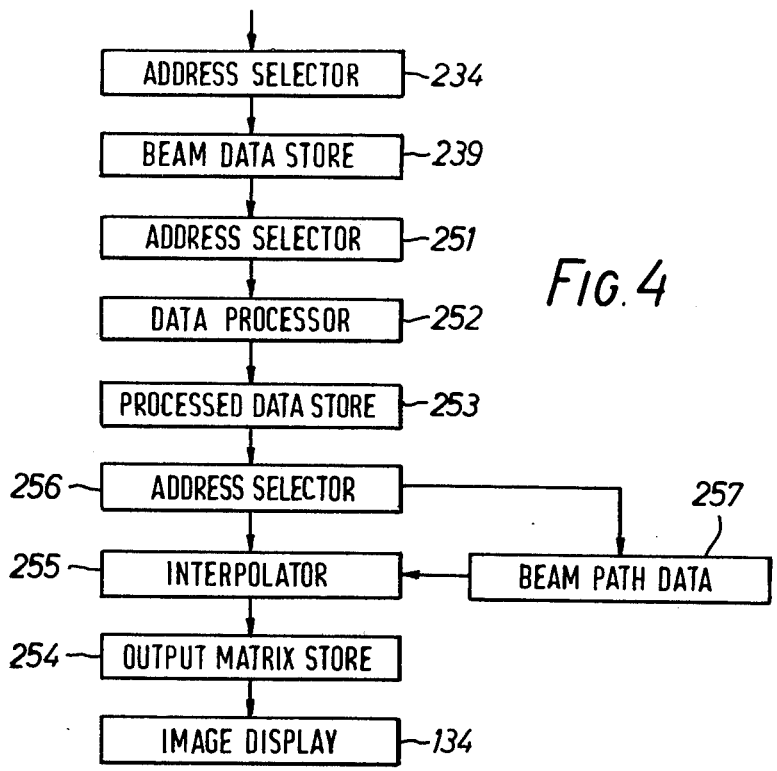

FIG. 4 sets out diagrammatically the general layout of the signal processor 50 indicated in FIG. 2. According to FIG. 4 the processor 50 comprises a beam data store 239, and each signal from the subtracting circuit 48 is written into this store 239, the signals as explained being expressed as logarithms in digital code. In this storage procedure the address in the store for each signal is selected by an address selector 234. With the completion of such logarithmic storage in store 239, data is drawn from this store in parallel sets by means of an address selector 251, and applied to a data processor 252. The nature and operation of the unit 252 will be described at length later, but for the moment it may be stated that the processing by the unit 252 leads to the production of what may be termed a corrected layergram. As the processing of each set takes place the processed data is stored term-by-term in a processed data store 253, the store having different sections each for accepting the data deriving from one respective set only. The apparatus further includes an output matrix store 254 in which the data, when all processing is complete, is held in a form in which it directly represents the distribution of absorption coefficient over the area of the cross-section examined. The addresses of the store 254 correspond to the meshes of a, for example, Cartesian meshwork, each mesh representing directly a particular elemental area of the cross-section examined, and all the meshes together extending without discontinuity so as to include all, at least, of the area of interest in the examined cross-section. At the address of each mesh there is finally stored a signal which represents, to the degree of accuracy permitted by the equipment, the absorption coefficient of the material of the body lying within the elemental area of the mesh concerned. When the storage is complete for all meshes, the image may be displayed by unit 134 comprising say a cathode ray tube, or printer, or additionally or alternatively magnetic tape storage means. As a high degree of accuracy is required in the image reconstruction, interpolation is performed by means of an interpolator 255 on transferring the processed data stored in the store 253 to the output matrix store 254. The interpolation is achieved by co-operation between an address selector 256 and a beam path data store 257 as will be described.

Before proceeding further with the description of the signal processor 50, the theoretical basis of the corrected layergram technique according to the invention will now be described, with reference to FIG. 5. In this figure the point 0 is any point in the plane of the exploring beam 21 at which the absorption of the material of the body under examination is required. Having ascertained the absorption at this point in the manner now to be explained in more detail the absorption at other points in the plane may be found in the same way thus building up an image of the absorption in the plane. The point 0 is assumed to be referenced with respect to the aforesaid Cartesian meshwork of the output matrix store, of which the axis Ox in the figure lies in the direction of the x-axis and Oy lies in the direction of the y-axis. For simplicity, the beam 21, in the successive positions during each lateral scan, at which its transmission is sampled, will be regarded as comprising a set of parallel beams. As already indicated, all of the beams are similar in cross-section, and the spacing of beams is uniform in any one set and the same for all sets. Moreover the sets lies with respect to one another in uniformly angularly spaced sequence.

An inaccurate method of ascertaining the absorption at a point such as 0 using such exploring beams is to sum the absorption suffered by all those beams that pass through the point 0. In the special situation that the absorption by material outside the relatively small region common to all the beams passing through the point 0 is relatively so small that it can be discounted, this sum approximates to the absorption in the immediate vicinity of the point 0. In practice, however, absorption outside the small region around 0 introduces errors into the method. The method is known as the layergram technique, the layergram of a set of beams with respect to a given point being understood to be proportional to the sum of the absorptions of all the beams which pass through the point. The corrected layergram technique which constitutes the basis of the invention depends on the principle that the error made in taking the simple layergram relative to the point 0 as a representation of the absorption at the point 0 includes a contribution due to the absorption at all points other than 0 of the beams passing through the point 0. Moreover the total error can be derived from the absorption of the beams not passing through the point O, and the error thus derived can be deducted from the simple layergram to correct it.

If $f(\theta v)$ is the absorption suffered by the beam passing through the point 0 at an angle $\theta v$ with respect to the axis Ox and there are $N + 1$ such beams in total at different angles, then the value G, of the layergram with respect to the point 0 of the beams of the explored plane is defined by $$G = \frac{\pi N}{N} \sum_0^N v f(\theta v).$$

If $\omega(x,y)$ is the absorption per unit length to the radiation used in the exploration, in the immediate vicinity of any point (x,y) in the exploring plane, x and y being the Cartesian coordinates of the point with respect to the notional Cartesian reference system, then $\omega(x,y)$ represents the distribution of absorption coefficient in the plane: moreover $$f(\theta v) = \int_{-\infty}^{+\infty} \omega(x,y) ds,$$

where $ds$ represents an element of distance along a beam and the integration is taken along the track of the beam at angle $\theta v$ as signified by the suffix $v$.

It may be shown that if dA is an element of area of the exploring plane located at the point (x,y) and if $s$ is restricted to signify the distance from the point 0 to the point (x,y) then $$C = \int \frac{\omega(x,y)}{s} dA,$$

where the integration extends over the whole of the plane except the singularity at the origin. Clearly if desired the integration may be regarded as taken over any number of separate areas of the plane if these areas in total cover the whole region of integration. In particular the integration can be regarded as covering a first area bounded by a circle centred upon the point 0, and as covering also a number of thin annuli also concentric with 0 and totalling in area all that of the rest of the plane. The integral over the $k$th annulus in order from the centre 0 can be represented $$\frac{1}{s_k} \int_k \omega(x,y) dA$$

in which $s_k$ is the mean distance of the annulus from 0. This assumes that the annulus is sufficiently thin. The integral represents the sum of the absorption of all the beams which pass through 0 due solely to their passage through annulus $k$. If it can be assumed that $\omega(x,y)$ has sensibly the same value $\omega_0$ over the whole of the first area then the integral over this area takes the value $$a = \frac{N+1}{N} \cdot \pi a \omega_0$$

given that $a$ is the diameter of the area and that all the beams pass symetrically through 0, all beams having a width small compared with $a$. However if the beams have a width of $a$, the intensity of radiation being sensibly uniform over their cross section, then $\alpha$ takes the different value $$\frac{1}{4} \cdot \frac{N+1}{N} \cdot \pi a^2 \cdot \omega_0,$$

regarding the beams as of unit thickness in a direction normal to the exploring plane. In either event it is shown that an expression can be derived for G which is of the form $$a + \sum_1^\infty \frac{C_k}{s_k}$$

if $$C_k = \int_k \omega(x,y) dA.$$

The assumption of symmetry in regard to the passage of exploring beams through the point 0 will not in general be wholly valid as the point 0 is selected at different locations in the exploring plane. It will in general remain true, however, as an approximation, and as will be pointed out in more detail later it may be made effectively valid for all locations by a suitable interpolation procedure.

On the general assumption that $\omega(x,y)$ nowhere changes senisbly in a distance of magnitude $a$, which implies that $\omega(x,y)$ is a frequency band limited function, it is possible to take all the annuli of width $a$, this width complying with the condition of thinness, so that writing $$s_k = ka,$$

$$C_k = C(ka),$$

the expression for G takes $$\alpha + \sum_{1}^{\infty} \frac{1}{ka} \cdot C(ka).$$

In the expression thus derived the term $\alpha$ is a measure of the required value, $\omega_0$, of the absorption function, namely that at the point 0. The remaining terms, those of the summation with respect to $k$, represent the error of the layergram method of ascertaining the value of $\omega_0$. The error can be cancelled, however, by taking into account the absorptions suffered by all the remaining beams of the exploration, that is to say those not passing through the central circular area contributing the term $\alpha$.

To develop the details of the corrected layergram technique, it is necessary to sub-divide into different classes the remaining beams, which do not pass through the central circular area of diameter $a$. This area may be termed zone 0, and the beams which pass through it may be termed beams of class 0. Around this zone is a thin annular area of mean radius $a$ which may be termed zone 1. Of the beams not passing through zone 0 there will be certain beams which alone pass through zone 1. Clearly each next surrounding annulus will distinguish a particular set of beams in the same way. In this way, calling the further annular zones 2, 3, 4, ... in the sequence of their distance from the origin 0 it can be said that the zones 0, 1, 2, 3, 4, ... distinguish the corresponding classes of beams 0, 1, 2, 3, 4, .... It will be evident that if, as has been assumed, there are N+1 beams in class 0, then there will be 2(N+1) beams in every other class. The angular distribution of the beams in any class is uniform following the assumptions initially made as to the character of the beams employed.

The beams of class 0 passing through zones of higher order will do so normally. As compared with this, beams of any of the classes 1, 2, 3, 4, ... on passing through any higher order zone will pass slantwise at an angle depending on the class of beam entailed. This is illustrated in FIG. 5, which shows a beam in class 0 passing through zone $k$ normally and shows a beam in class $j$ passing through zone $k$ at a characteristic angle. The beam absorption is thus correspondingly different as the interception of the zone by the class of beam is different. Whereas, therefore, the interception of zone $k$ by the beams of class 0 entails the degree of absorption represented by $$\frac{C(ka)}{ka},$$

the interception of the same zone by the beams of any other class $j$ will entail a corresponding degree of absorption that can be represented by $$2F_{jk} \cdot \frac{C(ka)}{ka}$$

the factor $F_{jk}$ allowing for the fact of the different angle of interception.

It will be realised that zone $k$ cannot be intercepted by any beam of class greater than $k$. Thus $$F_{jk} = 0, \quad J > k.$$

Moreover the overall absorption suffered by the beams of class 1 is $$2 \sum_{1}^{\infty} F_{1k} \cdot \frac{C(ka)}{ka},$$

whereas that suffered by the beams of class 2 is $$2 \sum_{2}^{\infty} F_{2k} \cdot \frac{C(ka)}{ka},$$

while the overall absorption for beams of class 3 is $$2 \sum_{3}^{\infty} F_{3k} \cdot \frac{C(ka)}{ka},$$

and so on.

It follows that the value of the expression $$\sum_{-\infty}^{+\infty} \mu L_\mu \, s_\mu$$

in which $$s_{-\mu} = s_\mu = \sum_{\mu}^{\infty} F_{\mu k} \cdot \frac{C(ka)}{ka},$$

and the factors such as $L_\mu$ are a set of coefficients such that $$L_{-\mu} = L_\mu,$$

$$L_0 = 1,$$

reduces simply to the value $\alpha$, provided that $$0 = 1 + 2L_1 \cdot F_{11}$$

$$0 = 1 + 2L_1 \cdot F_{12} + 2L_2 \cdot F_{22}$$

$$0 = 1 + 2L_1 \cdot F_{13} + 2L_2 \cdot F_{23} + 2L_3 \cdot F_{33}$$

... and so on.

The set of coefficients $L_\mu$ is clearly determined by these equations.

The equations can be solved for the series $L_1$, $L_2$, $L_3$, ..., if the intercept factors of which $F_{jk}$ is typical are first of all determined. The summation of all such terms as $L_\mu S_\mu$ between the limits $\pm \infty$ can then be carried out to yield the measure of the absorption function at the point O. The factors $L_\mu$ may be termed zonal weighting factors, or more simply L-factors, since for example $L_\mu$ multiplies the absorption suffered by beams of the class $\mu$ distinguished by the zone $\mu$.

In principle, the L-factors can be calculated exactly provided the intercept, or F-factors are known exactly. The F-factors depend not only on beam geometry but also on the assumption made as to distribution of intensity of radiation over the cross section of the beam. As previously indicated the intensity of radiation will not in general be uniform over the beam width since in most practical cases there will be a "scanning aperture" effect, though it may be possible to regard the intensity as sensibly uniform over the beam thickness. For practical purposes the F-factors, and thus the L-factors can be sufficiently approximated in a variety of ways based on different assumptions depending on the physical parameters of the scanning system. Some of these ways will now be described.

Figure 5:
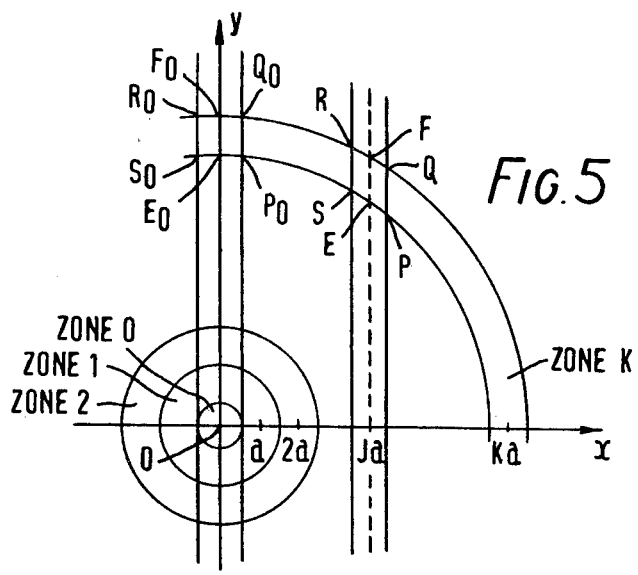
FIGS. 5 and 6 are diagrams explanatory of the method of operation of the circuit of FIG. 3.

In FIG. 5 the zone O is shown as the area within the innermost of the circular perimeters drawn with the point O as centre, the zone having perimeter radius equal to $\frac{1}{2}a$ as indicated earlier. Lying immediately outside zone 0 there is shown the first annular zone, namely zone 1, having mean radius $a$ and width equal to $a$. Other surrounding zones are not shown apart from zone $k$ as typical, this zone having mean radius ka and like all annular zones the radial width $a$.

One beam of class 0, assuming it to be a very thin beam, may be regarded as represented by the Oy axis of the figure, this beam intercepting the $k$th zone as shown for the extent of its length represented by $E_OF_O$. A beam of class $j$ of the same thin cross-sectional dimensions is also shown and is represented by the broken line parallel with the Oy axis drawn at distance $ja$ from this axis. The beam intercepts the $k$th zone as shown for that extent of its length represented by EF. In those circumstances the value of the intercept factor $F_{jk}$ is given by the length of the intercept EF divided by the length of the intercept $E_OF_O$. This ratio represents the increase of absorption suffered by beams of class $j$ in passing through zone $k$ as compared with beams of class $O$. It is not necessary that the beams should be infinitely thin for this ratio to be valid, but this method of approximating the F-factors gives good results for the L-factors if the effective beam width is small compared with the annular width $a$ which is determined by the separation of adjacent parallel beams.

If the beams can be assumed to be of uniform cross sectional intensity and of a width equal to the annular width $a$ the F-factors can be evaluated on the following basis. In FIG. 5 a beam of class 0 is shown as bounded by the parallel lines $P_OQ_O$ and $S_OR_O$ which are furthermore tangential to the perimeter circle of zone 0. An example of a similar beam of class $j$ is represented by the bounding parallel lines PQ and SR which intersect the Ox axis at co-ordinate distances $(j+\frac{1}{2})a$ and $(j-\frac{1}{2})a$ respectively. The first of the beams referred to intercepts the $k$th zone over the area $P_OQ_OR_OS_O$ while the second has the intercept areas PQRS. In the circumstance of such beams the value of the intercept factor $F_{jk}$ is the ratio of the latter area, PQRS, to the former $P_OQ_OR_OS_O$. This is true on the assumption, as aforesaid, that the beams are sensibly uniform in intensity over their cross-section and that the degree of absorption is sufficiently small.

The application of these two methods of deriving L-factors forms the subject matter of co-pending British Application Nos. 38817/73 and 39070/73 in the name of E M I Limited, the inventor being J. E. Best.

In accordance with the present invention another approach to the processing of absorption data by corrected layergram methods will now be given with reference to FIG. 6, this being the approach adopted in the apparatus which is described and illustrated.

In this figure, as in FIG. 5, the point O is a point in the plane of the exploring beams at which the absorption of the material of the body under examination is presupposed to be required. Again this point is assumed to be referenced with respect to the aforesaid Cartesian meshwork, the axis Ox in the figure lying in the direction of the x-axis of this meshwork and the axis Oy lying in the direction of the meshwork y-axis.

Figure 6:
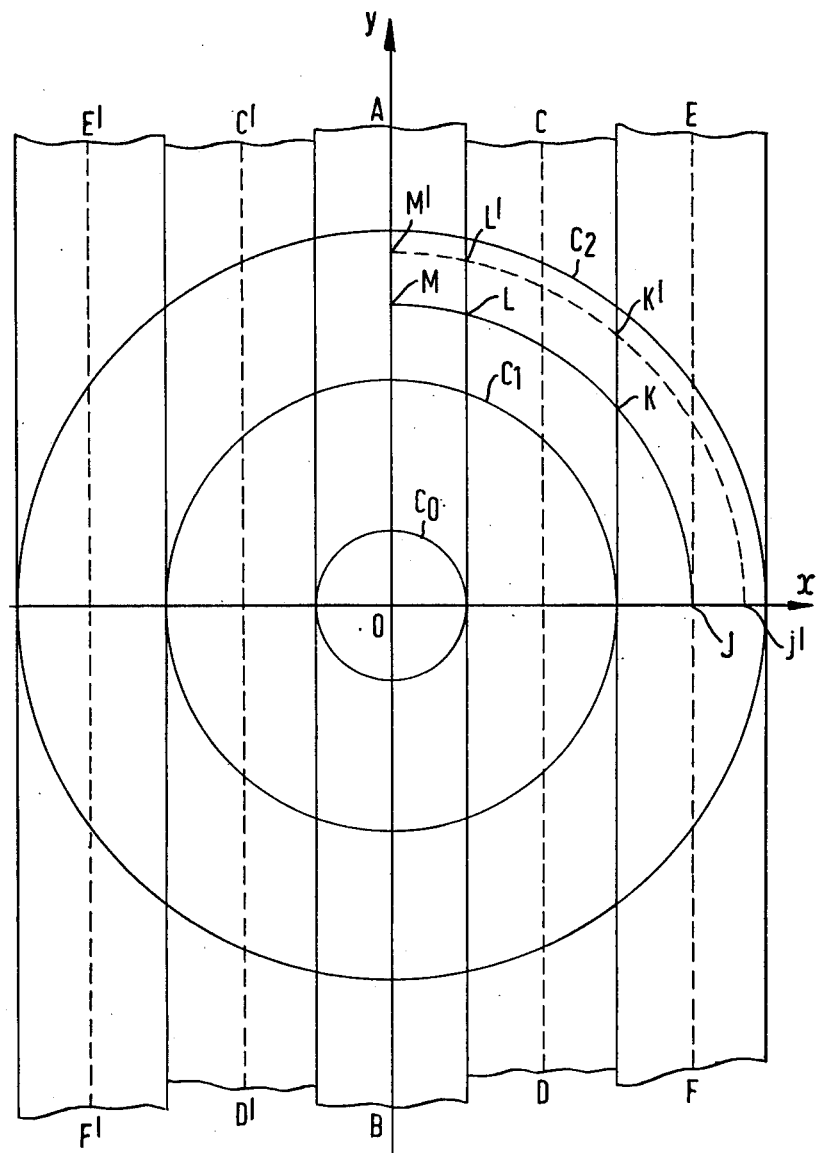

FIG. 6 shows five beams AB, CD, C'D', EF and E'F' of that parallel set of beams whose angular position in the plane is such that their axes lie parallel with, or sensibly parallel with, the axis Oy. Let it be assumed initially that the beams are all of identical cross-section and of width $a$. It is supposed that the centre line of the beam AB is the axis Oy. The centre lines of the other beams are shown in broken line. Furthermore the circles $C_O$, $C_1$ and $C_2$ drawn in the diagram concentrically about the point 0 are of radii $\frac{1}{2}a$, $3/2a$, and $5/2a$ respectively, and the sequence is assumed to continue after this fashion.

Although FIG. 6 shows only beams of one particular parallel set, it must be imagined that the beams of all the other angularly disposed sets are also present. Thus if $N+1$ is the total number of such parallel sets it must be imagined that whereas only one beam is shown intercepting the area of circle $C_O$, namely the zone 0, there are $N+1$ beams intercepting this zone in identical manner apart from difference of angle. The number $N+1$ may, with advantage in relation to the image reconstruction, be selected as of the order of $\pi$ times the number of beams per set. Interception such as assumed is ideal in the sense that the centre lines of all the beams intercepting the zone 0, pass through the point 0. With different selections of the point 0 in the plane of exploration this ideal can in general only be approximated by suitable interpolation between the absorption data of adjacent beams.

The area outside of circle $C_O$ lying within circle $C_1$ is again termed zone 1, and of all the beams not intercepting zone 0, $2(N+1)$ beams intercept zone 1. These are again the beams of class 1. On the ideal assumption made in regard to the beams intercepting zone 0, the centre lines of the beams of class 1 will lie tangentially to a circle center 0 and radius $a$. Moreover on the assumption of uniform angular disposition of parallel sets, the angular dispositions of the exploring sets of beams are those of the uniform angular series.

$$0, \frac{\pi}{N}, \frac{2\pi}{N}, \frac{3\pi}{N}, \ldots, \frac{(N-2)\pi}{N}, \pi,$$

and the tangent points will lie uniformly and correspondingly distributed round this circle.

The area outside of circle $C_1$ but lying within circle $C_2$ is once again termed zone 2 and the beams in class 2 consist of all the beams, excluding those classes 0 and 1, which intercept zone 2. The beams of this class are also $2(N+1)$ in number and ideally distributed in relation to a circle radius $2a$, centre 0, in the same manner as the beams of class 1.

Classification, as in the case of FIG. 5, of the beams lying in the exploring plane may be continued in this fashion so setting up a series of classes of beams in the order in which they are classified in sequence, namely, classes 0,1,2,3,4, ... corresponding to the zones 0,1,2,3,4, ...

As already explained, if the only absorbing region in the exploring plane was located within the zone 0 then the sum of the absorptions suffered by all the various beams of class 0 would constitute a true measure of the absorption of this absorbing region. In practical cases, however, the sum of the absorptions of the beams of class 0 will not in fact constitute an accurate measure, since the beams will pass through other absorbing regions outside zone 0. The general principle, as described, of weighting total zonal beam absorptions by corresponding L-factors and summing may, however, be applied, and in this approach the L-factors may be approximated in the following way.

Assume that the absorption of this material of the body in the plane of the beams is everywhere zero except in a single area of such small size that no dimension of it cannot be regarded as very small in relation to the beam-width dimension $a$, this area moreover not lying within zone 0, but lying in any other zone. On this assumption, the summing of all the weighted absorption totals must yield the result zero wherever the area is located if the L-factors are rightly chosen. This leads to a set of equations which on solution gives the required L-factors.

As will be realised the number of beams in any class contributing absorption to the overall summation for a given location of the small area will be the number of beams of that class intercepting the area. On the assumption that the beams are of sensibly uniform intensity over their cross-section, and that the degree of absorption is sufficiently small, any absorption total apart from weighting will moreover be simply proportional to the number of beams intercepted by the area. If, for example, the area lies in zone 2 the number of beams of class 1 contributing absorption to the overall summation when the area is so located is the number of beams of class 1 overlapping, that is to say intercepting, the area as located; and the absorption contribution to the overall summation prior to weighting by the L-factors for beams of class 1 is simply proportional to this number of beams. This leads to the expression of the unweighted absorption contribution as proportional to the length of arc, concentric to the centre 0, and passing through the small absorbing area, which lies within a beam of class 1. On this basis the equations may be set out for deriving the L-factors provided some assumption is made as to the radial distance of the small absorbing area from the centre O. For example it may be assumed that, in whatever zone the small area is located, it is situated at the mean radius for the zone.

It will be realised that if some other radius, intermediate the extreme radii of the zone of location, were selected then different arc lengths of interception would be involved and correspondingly L-factors would be derived similar to, but not identical with, those based on the mean radius location.

In illustration of such differences, consider the quadrant of arc JKLM of radius $2a$ shown in FIG. 6, and assume that the small area is located within zone 2 on this arc. Beams of class 2 would then make an unweighted total absorption contribution proportional to the length of arc JK, that is to say the length of the arc JKLM intercepted by the beam EF of class 2. At the same time beams of class 1 would make an unweighted total absorption contribution proportional to the length of arc KL, that is to say the length of the arc JKLM intercepted by the beam CD of class 1. Beams of class 0 would make a corresponding contribution proportional to the length of arc LM, namely the length of arc JKLM intercepted by the half width of beam AB of class 0. The half width intercept takes account of the fact that the total number of class 0 beams is only half that of all other classes. On the reasoning that has been given the arc lengths JK, KL, LM determine the values of the F-factors $F_{12}$ and $F_{22}$, and so on for all the F-factors. If the small area were, however, situate at some intermediate zonal radius other than the mean radius OJ, say at the radius OJ' of the arc J'K'L'M' where J', K', L' and M' indicate new intercepts corresponding to the intercepts J,K,L,M then the new arc lengths J'K', K'L', L'M' would determine the F-factors $F_{12}$ and $F_{22}$ differently, with consequent different if similar values for the L-factors.

In practice, if the series of zonal factors is based on the location of the small area at mean zonal radius, then the series of factors $L_1, L_2, L_3 \ldots$ yield reconstructed images which tend to emphasise boundaries and transitional regions. On the other hand it is found that if the small area is located at a greater radius, for example, if it is located midway between the mean radius and the outer radius of the zone then this emphasis is virtually removed. With location midway between the mean and outer radii the lower order L-factors have values as follows:

$L_0 = 1.000$
$L_1 = -0.355$
$L_2 = 0.053$
$L_3 = 0.0258$
$L_4 = -0.0146$
$L_5 = -0.0093 \ldots$ whereas if the small area is located at the mean zonal radius the first three L-factors are 1.000, −0.500, +0.060.

If the radial location of the small area within an annulus is specified by $\beta$, defined as the ratio of the radial offset of the small area from the inner boundary of the annulus to the difference in radius of the inner and outer boundaries then the last mentioned series may be described as that for which the value of $\beta$ is equal to 0.50; whereas the series first referred to is produced by setting the value of $\beta$ equal to 0.75.

It is not necessary that the value of $\beta$ should be constant throughout the whole range of the zones entailed. It may for example progressively diminish the higher the order of the zone, and may say have the value 0.75 for zone 1, thereafter diminishing asymptotically to the value 0.5, which it virtually attains for the highest order zone.

The foregoing analysis of FIG. 5 and 6 proceeds on the assumption that the function $\omega(x,y)$ representing the distribution of absorption co-efficients of the plane of interest is frequency band limited so that variations of the absorption of the beam 21, assumed to be thin, during any one lateral scan, do not occur at a rate exceeding a particular spatial frequency relating to the distance $a$. In practice of course the function $\omega(x,y)$ is not necessarily band limited to such an extent and when, as is possible, there are present spatial frequencies in excess of the frequency corresponding to a wave length equal to twice the sampling interval $a$, errors can occur in processing which can give rise to substantial errors in the reconstructed image. In the practical form of the invention illustrated in FIGS. 1, 2 and 3 sampling is carried out however in such a way as to reduce such errors. As previously stated, sampling is effected by virtual beams of widths substantially equal to twice the separation between adjacent beams so that there is a substantial overlap of the adjacent beams. Moreover each virtual beam has a substantially sinusoidal intensity distribution across its width. It can be shown that this introduces frequency band limitation in the acquired data. The sinusoidal distribution represents an approximation to the central positive region of an intensity distribution of the form $$\frac{\sin \frac{\pi x}{a}}{x}$$

where $a$ is the sampling interval, and, to the extent that the approximation applies, it has the effect of band limiting the explored data to eliminate undesired components of high frequency.

If as has been assumed $a$ is the zonal width, and if $x$ represents distance from the beam centre line, then in the range $$-a \leq x \leq +a$$

the distribution of beam intensity according to FIGS. 1, 2 and 3 is approximately of the form $$\frac{1}{2} + \frac{1}{2} \cos \pi \frac{x}{a}$$

The beams may be made to conform closely to this form or other desired forms by the introduction of an appropriate distribution of absorbing material across the path of each beam, but it is found in practice, that for normal purposes it is not necessary, assuming the sinusoidal form, to utilise this additional technique to achieve sufficient accuracy.

It has been found that taking a value of $\beta$ equal to 0.625 yields L-factors which, with beams of approximately sinusoidal distributions of radiation intensity as described, give a satisfactorily high degree of accuracy in the reconstructed image, for example an accuracy of the order of 1 part in 1000 at each image point. With this value of $\beta$ there is some degree of overshoot with transitions, or edges, in the image reconstruction, but this degree is only slight. The first twenty L-factors of the series are indicated in the table comprising FIG. 7. The series is continued to as many factors as are required to compensate for absorption out to the boundaries of the image whatever the position of the elementary area of image undergoing reconstruction.

In the series of FIG. 7 the factor $L_{40}$ is just in excess of $-0.0001$ but although very small, factors of this and even smaller magnitude continue to be significant for accurate image reconstruction, bearing in mind that they multiply the sum of the absorptions suffered by many beams, about 180 in the example being considered. Even for relatively inaccurate image reconstruction intended to give a general picture the number of L-factors should be about half the number of beams in each set. Generally speaking and apart from a small perturbation affecting the early terms of the series, the factors (apart from $L_O$) for the case of $\beta$ equal to 0.625 fit a monotonic function which is always negative and approaches zero assymptotically, being slowly varying after the first few terms. The kind of perturbation mentioned is an oscillatory component and it is manifested for $\beta = 0.625$ by the fact that $L_4$ is numerically less than $L_5$. A corresponding perturbation is not noticeable for $\beta$ equal to 0.75, but is even more pronounced for $\beta$ equal to 0.5. A perturbation such as discussed will not noticeably affect the L-factors after $L_5$. As a general characteristic, the L-factors (apart from $L_O$) approximate to a monotonic negative function whether or not the beam width is small compared with the separation of adjacent parallel beams or is comparable with this separation. Strictly speaking on the principle that $L_{-\mu} = L_\mu$, as earlier set out, the function is symmetrical about $L_O$ and both halves are monotonic about $L_O$, apart possibly for the aforementioned small parturbation.

It appears that variations in the value of B have an effect similar to that of aperture correction. Thus, values of $\beta$ close to 0.5 tend to give marked overshoot in the image reconstruction in response to a step function in the absorptions of the body.

A desired degree of overshoot is often desirable from the standpoint of delineation of detail, though it may result in some reduction of numerical accuracy in the vicinity of the step functions, that is to say from the standpoint of determining within specific limits the magnitude of the absorption in the vicinity of a given point in the cross section, when this point lies in the close neighbourhood of rapid changes in absorption. On the other hand it is found as a general rule that if the value of $\beta$ materially exceeds 0.75 then conditions corresponding to undershoot tend to exist. The practical range for $\beta$ lies within the limits 0.5 to 0.75, though in rare cases if a special effect is desired $\beta$ may be situated outside these specified limits. Aperture correction can also be simulated by suitable adjustment of the L-factors produced on the basis of other approximations mentioned in this specification.

The general procedure that has been described, and which as has been indicated is a layergram correction technique, may be viewed in the light of a sequence of successive approximations made zone by zone. If for example the absorption of the material of the cross section is zero outside of zone 1 through finite otherwise, it will be evident that the error in the simple layergram evaluation for the absorption within zone 0 is compensated by the factor $L_1$ when this is multiplied by the total absorption of beams of class 1. On the other hand if finite absorption extends instead as for as to the outer boundary of zone 2 the $L_1$ correction is insufficient, and must be supplemented by $L_2$ correction on the same pattern. Continuing in this way and bringing in zone after zone it is evident that the method may be thought of in general terms as one that approaches always more closely to the true result as each zone is introduced into the computation. If the absorption vanishes beyond the $n$th zone then the series of L-factors corrections must be continued as far as the factor $L_n$ to obtain the true result. The absorption is of course assumed to be zero beyond the boundaries of the reconstructed image.

In the actual determination of the series set out in FIG. 7, each given beam of sinusoidal distribution was assumed to have the same effect as a number of contiguous and relatively fine beams extending over the whole width of the given beam. Each fine beam was considered to be of uniform intensity across its width, but the intensities of the fine beam were assumed to correspond to successive points on the intensity distribution curve of the given beam. L-factors were assigned, on the theory outlined, to the corresponding fine beams, assuming a value of $\beta = 0.625$ in each case. These factors were then also multiplied by the respective fine beam intensities to produce a series of contributions that were then added to derive the resultant L-factors for each of the given beams having the sinusoidal intensity distribution.

Having decided upon the use of a particular series of L-factors and having acquired beam absorption data in parallel sets, and in logarithmic form, as earlier described in relation to FIGS. 1 and 2, the processing to be performed by the unit 252 of FIG. 3 may be accomplished by means of an appropriately programmed computer. It is to be noted that according to the theory that has then given, the absorption suffered by all the beams of a given class defined in relation to a given point in an elementary area with which the absorption coefficient of the material is to be evaluated, is totalled and the total multiplied by the respective L-factors. The sum of such weighted totals for all classes (defined in relation to the given point) is then proportional to the required absorption coefficient. A procedure on these lines is similar in principle to the convolution processing indicated in the aforesaid paper by Ramachanadran et al. The theoretical basis of the present invention is however different from that described in the paper, and the L-factors employed in accordance with the present invention conform to a substantially different function from the convolution function arrived at in the paper. They yield moreover substantially improved results. Nevertheless it is reasonable to regard the signal processing in apparatus according to the invention as a special form of convolution or inversion processing. Moreover in accordance with a feature of the invention, as will now be described, the beams are taken in parallel sets and as distinct from the convolution set by set with respect to a given evaluation point, as in said paper, all the beam absorption values in every set are individually subjected to multiplication by the L-factors series. The products so produced are sorted into different addresses in different sections of the processed data store 253, there being one section for each parallel set of beams, and one address in each section corresponding to the center line of each beam in the respective parallel set. Each address accumulates a whole series of products. The totals accumulated in the store 253 are then distributed to different addresses in the output matrix store 254 to build up the required representation of the absorption distribution in the area of examination. This replacement of what is primarily a two-dimensional convolution procedure for every evaluation point taken one at a time by one which is a series of linear convolution procedures for all the beams of all the sets with respect to all evaluation points, followed by selective summation, has special advantages in speed of operation, and also lends itself to the use of a particular form of special purpose computer, which will be subsequently described for performing the linear convolution processing. This special computer further increases the speed of operation. The method also facilitates interpolation in evaluating the absorption for each mesh of the Cartesian meshwork represented by addresses in the output matrix store 254.

Figure 8:
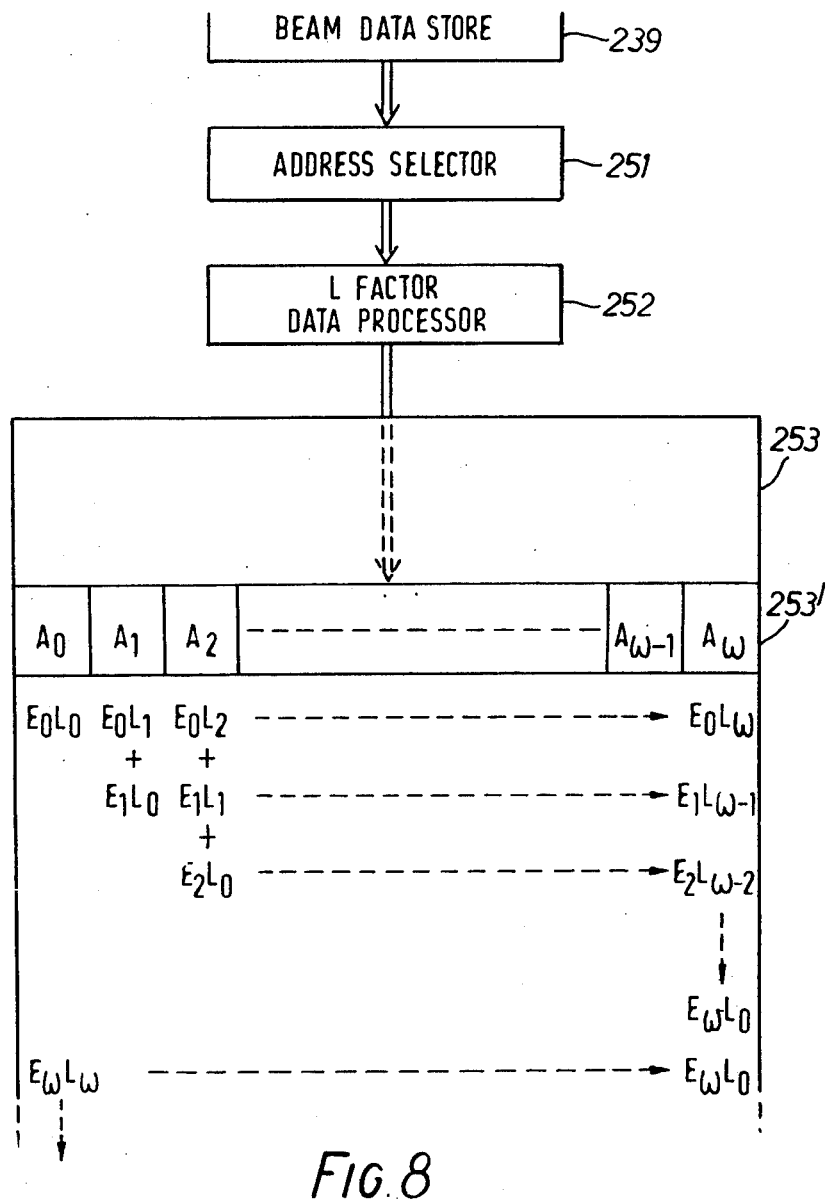
FIG. 8 is a more detailed block diagram of part of FIG. 3.

The sequence of linear procedures will first be considered in detail, and with the aid of the simplified block diagram of FIG. 8.

In FIG. 8 the numeral 239 again designates the store from which beam absorption data is stored in the form of parallel sets as already referred to, the store accepting the data in logarithmic form is indicated in FIG. 4. The address selector 251 for deriving outputs from the store 239 is also depicted, as is the processed data store 253 holding processed data from the convolution processor 252 now to be understood as operating after the linear convolution manner.

To consider the use of the store 253, suppose that the absorption data values relative to the exploring beams of a parallel set are $$E_0, E_1, E_2, E_3, \ldots$$

respectively in the order in which the beams occur across the set. Moreover suppose that the sequence of terms $$L_0, L_1, L_2, L_3, \ldots$$

is the sequence constituting the L-factors series, and consider that the value $E_0$ has been drawn from the store 239. This value is multiplied separately by each of the terms of the L-factor series in the data processor 252 and the products $$E_0L_0, E_0L_1, E_0L_2, E_0L_3, E_0L_4, \ldots E_0L_\omega$$

are respectively stored at addresses $$A_0, A_1, A_2, A_3, A_4, \ldots, A_\omega$$

in section 253' of the processed data store 253 under the control of the address selector 251. Then consider the value $E_1$ to be withdrawn from 239 and likewise multiplied by the terms of the L-factor series 252, to produce the products $$E_1L_0, E_1L_1, E_1L_2, E_1L_3, \ldots, E_1L_{\omega-1}$$

These products are stored respectively at the addresses $$A_1, A_2, A_3, A_4, \ldots, A_\omega$$

in section 253' of the store 253, being added to the products already stored at these addresses. Next, withdrawing the value $E_2$ from the store 239 and following the same multiplication procedure, the products $$E_2L_0, E_2L_1, E_2L_2, \ldots, E_2L_{\omega-2}$$

are stored respectively and additively at the addresses $$A_2, A_3, A_4, \ldots, A_{\omega'}$$

The process is continued in this way until all the absorption values of the parallel set have been used up. When this stage is reached the magnitude stored in address $A_0$ will be $$S_0 = E_0L_0,$$

that in address $A_1$ will be $$S_1 = E_1L_0 + E_0L_1,$$

that in address $A_2$ will be $$S_2 = E_2L_0 + E_1L_1 + E_0L_2,$$

that in address $A_3$ will be $$S_3 = E_3L_0 + E_2L_1 + E_1L_2 + E_0L_3,$$

and so on, following this pattern.

In a next stage of the procedure, the absorption values are drawn from the store 239 in a like way, but in the reverse order to that in which they were previously taken. As so taken in reverse order, they are processed in identical manner as before except that the addresses in section 253' of the store 253 are also used in the reverse order. This is depicted in FIG. 8.

Finally the values $$E_0L_0, E_1L_0, E_2L_0, E_3L_0, E_4L_0, \ldots, E_\omega L_0$$

are subtracted respectively from the magnitudes already accumulated at the addresses $$A_0, A_1, A_2, A_3, A_4, \ldots, A_\omega$$

to yield an ultimate set of magnitudes at these addresses. This procedure is continued for the absorption values corresponding to every parallel set of beams, the set of magnitudes for each set of parallel beams being accumulated in a different section of the store 253. The preferred final processing of the accumulated magnitudes to yield the required image reconstruction will be referred to subsequently. The process which has been described of accumulating magnitudes may be described as deriving for each beam data signal a summation signal which when used to form a layergram produces a compensated layergram.

Figure 9:
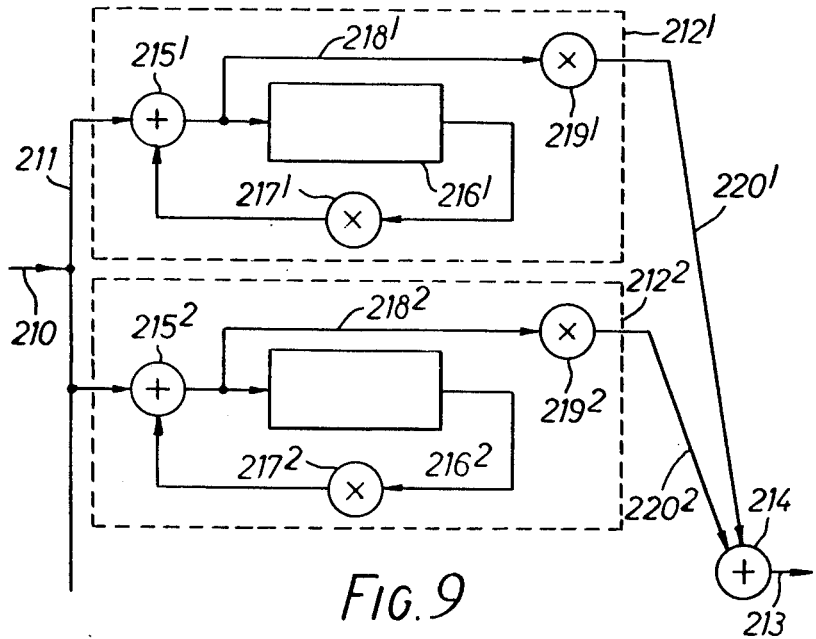
FIG. 9 illustrates one practical form of data processor, in accordance with an example of the invention, as used in the circuit of FIG. 7.

The series of operation which is depicted with reference to FIG. 8 can be carried out by a suitable programmed digital computer, but in the present example of the invention, the L-factor data processor takes the form of a special computer in which the L-factors are generated implicity in the terms of a time series produced by circuits which also perform the multiplication generating the products which are transferred to the store 253. This can be done since all or most of the L-factors can be approximated as a limited set of exponential terms, this being possible since the L-factors approximate in general to a slowly varying monotonic function. FIG. 9 of the accompanying drawings shows the general form of a circuit operating on these lines.

In this figure, 210 is a path carrying beam absorption data in digital form as withdrawn from the beam data store 239 of FIG. 8 by the address selector 251. From 210 this data is distributed via path 211 to the inputs of a number of similar circuits such as those included within the rectangles shown in broken line and designated 212[1] and 212[2]. The outputs of these circuits also in digital form are fed to the common output path 213 via the adder circuit 214 and the transformed data as it appears at conductor 213 is suitable for transfer to, and storage in, any section such as 253' of the store 253 of FIG. 8 in accordance with the procedure outlined with reference to that figure. The generation and character of these contributions will become more clear with the description of the circuits such as 212[1] and 212[2].

Considering circuit 212[1] as typical of these circuits, an absorption data signal appearing on path 210 is fed via 211 to the adder circuit 215[1] and thence to the input of the digital delay line 216[1], from which the signal emerges with a delay equal to the period between clock pulses of a master clock pulse source used to control all the circuits 212[1], 212[2], . . . . The use of such clock pulse sources is well known and has not been illustrated. The initial absorption data signal is timed so that its appearance on the path 210 is synchronised with an initial, or reference, clock pulse for one parallel set. Assuming this is the signal $E_0$ referred to above, the other signals $E_1$, $E_2$ etc. of the parallel set appear on the path 210 synchronously with successive clock pulses. The signal emergent from the delay line 216[1] is applied to multiplier circuit 217[1], which multiplies the signal by a numeral less than unity, and feeds the signal so multiplied back to the adder circuit 215[1] via the other of its two inputs, thence to be applied again to the input of the digital delay line 216[1]. The signal then recirculates the loop 216[1], 217[1], 215[1], to perform a further recirculation, and so on for a number less one of times equal to the number of data signals forming a parallel set and therefore for the number of L-factors utilised after Lo. The output from the circuit is taken from the output of the adder circuit 215[1] and applied via conductor 218[1] to the multiplier circuit 219[1].

The output of the multiplier 219[1] is applied to the input of the adder circuit 214 via path 220[1], where the output is added to that of circuit 212[2] and the output of other such circuits. As signals appear in the output of the adder circuits 215[1], 215[2], . . . , with the occurrence of successive clock pulses, a series of signals is fed out via path 213. When the series has continued for a time specified by the number of L-factors utilised it can be terminated by clearing the delay lines of the circuits 212[1], 212[2], . . . , and a new series can then be started.

In regard to the operation of the group of cicruits 211[1], 212[2], . . . , consider the operation of any one of them, say circuit 212[k]. As indicated the absorption data signal applied to the group to start the generation of the series of signals at the group output conductor 213 is of value $E_0$. Then considering only the subsequent history of the signal $E_0$, it may be shown that the output of the circuit 212[k] via its output conductor 220[k] at a time $r$ clock pulse periods after the application of the signal $E_0$ that is at clock pulse $r + 1$ is of value $$E_0 B_k e^{a_k r}$$

in which the expression $$a_k = \log_e A_k,$$

where $A_k$ is the multiplying factor, less then unity, of the multiplier 217[k] of the circuit 212[k], and $B_k$ is the multiplying factor of the multiplier 219[k] of the circuit. It there are $n$ circuits of which the circuit 212[k] is typical then at the time mentioned, which may be referred to as time $t(r)$, the output at conductor 213 due to the application of the signal $E_0$ to the circuit must be of value $$E_0 \sum_{1}^{n} {}_k B_k e^{a_k r} = E_0(r)$$

Thus the circuit of FIG. 9 can be made to generate the series of signals $E_0(r)$ at the times $t(r)$ consequent upon the application of the signal $E_0$. It is found that by suitable choice of the multiplying factors such as $A_k$ and $B_k$, the series of signals $E_0(r)$ synchronised with the successive clock pulses may be made to approximate numerically to a high degree of accuracy, at least for all values except a few initial terms, to the series $$E_0L_0, L_0L_1, E_0L_2, \ldots, E_0L_r, \ldots,$$

where the L's are the series of L-factors for the system. A few early terms of the series $E_0(r)$, namely say $E_0(1)$, $E_0(2)$, $E_0(3)$, may not correspond sufficiently accurately to the required values $$E_0L_1, E_0L_2, E_0L_3,$$

due to the initial factors $L_1$, $L_2$ and $L_3$ being not sufficiently accurately approximated, but they may be made to do so by adjustment, and such limited adjustment is simple in terms of operation of the digital computer.

Five circuits such as $212^k$ are used, it being found in practice that if $n = 5$ then with the exception of a few early terms which may be corrected as indicated, all terms may be generated with an accuracy corresponding to that in the final image reconstruction of about one part in a thousand.

It will be understood as has been indicated that, in the use of the circuit of FIG. 9, the absorption data signals of a parallel set of beams are fed in turn, as they occur across the set, to the input of the circuit of FIG. 9, a fresh value being applied with the timing of each clock pulse. When the circuit is so operated it generates at its output, and with each clock pulse, the terms of a series such as the series $$S_0, S_1, S_2, S_3, \ldots$$

described earlier. In conformity with this earlier description when the series is completed and the delay lines have been cleared, the same set of absorption data signals is fed into the circuit again by the address selector 251, but in the reverse order to generate another such series. With the generation of each of the series, the terms of the series are fed to the store 253 in the way earlier explained. Finally signals proportional to $$E_0L_0, E_1L_0, E_2L_0, E_3L_0, E_4L_0, \ldots$$

are fed to the addresses of the store so that the convolution process is completed correctly. These operations are all controlled and carried out in known manner by the digital computer, of which the circuit of FIG. 9 is a part. Thus the store section concerned, say 253', is finally filled for transfer to the output matrix store 254, the step by step accumulation being accomplished by the recirculations of the data in the circuit of FIG. 9.

With regard to possible errors in the values of $L_1, L_2, L_3$ these errors if significant are preferably dealt with as follows. Assume that the errors are respectively $$\Delta L_1, \Delta L_2, \Delta L_3,$$

then these errors are stored in the digital computer. Assume also that some beam datum value $E_j$ has been applied to the circuit of FIG. 8, the suffix $j$ signifying that the datum is relevant to the $j$th beam of a parallel set. Then a correction of value $$E_j \Delta L_1$$

is fed additively by the computer to store at the addresses $A_{j-1}$ and $A_{j+1}$ of the store section corresponding to the set. Moreover the correction value $$E_j \Delta L_2$$

is fed likewise to the store section at addresses $A_{j-2}$ and $A_{j+2}$. Likewise the correction value $$E_j \Delta L_3$$

is similarly fed to addresses $A_{j-3}$ and $A_{j+3}$. The principle of this procedure is followed for all values $j$ of the set and for all sets.

While processing of the sets of data according to FIG. 9 may be performed in a serial mode, taking parallel sets of absorption data in turn and applying them to a single processor of recirculation type as in FIG. 9, all these sets may be processed simultaneously in parallel by providing and programming a separate recirculation type circuit for processing each parallel set of data. This can give very rapid processing of the data, if this is required.

Although the invention is preferably carried out using the digital delay circuit of FIG. 9, it may also be carried out without the actual use of such circuits by employing a standard computer to simulate them. The time saving in processing may not then be so great, but is nevertheless useful.

Figure 10:
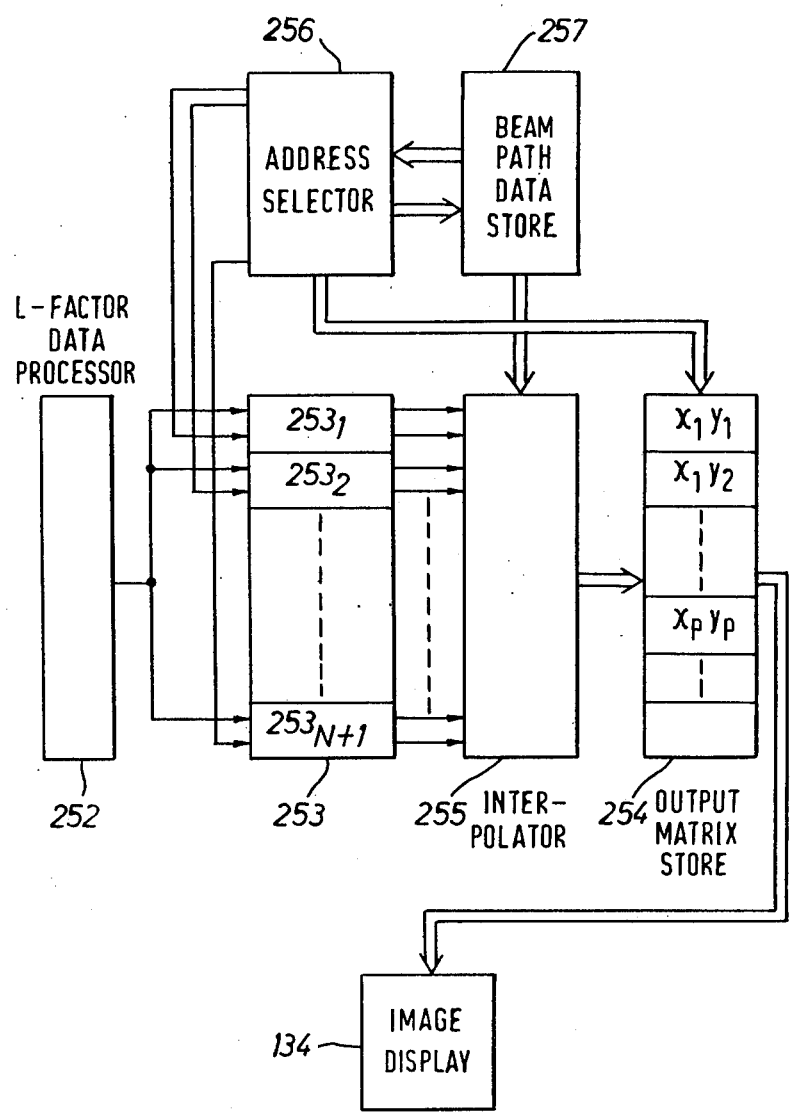
FIG. 10 is a more detailed block diagram of another part of FIG. 3.

FIG. 10 illustrates a block diagrammatic form, the circuit for transferring the magnitudes such as those finally stored in the address $A_0, A_1 \ldots$ referred to in the description concerning FIG. 8 from store 253 to the output matrix store, namely the store designated 254 in FIG. 4. During this transfer the interpolation earlier mentioned in relation to FIG. 4 is carried out. This interpolation conforms to a sinusoidal law. While it is possible to use linear interpolation the choice of the sinusoidal law is preferred in view of the approximately sinusoidal character of the distribution of radiation intensity across the beams.

In FIG. 10, the block 252 again represents the L-factor processing circuit. Assume that the absorption date to be processed falls into N+1 parallel sets, then the processor circuit 252 is assumed to comprise N+1 separate recirculation type circuits as disclosed with respect to FIG. 9, one respective to each set, so that all N+1 sets can be processed simultaneously. The products of L-factor weighting with respect to the various sets are stored in the sections $253_1, 253_2, 253_4, \ldots 253_n$ of the store 253, one section serving in relation to one respective recirculation type L-factor weighting circuit.

The data stored in these stores has to be transferred after sinusoidal interpolation to the final output matrix store 254. The transfer is performed under the control of an address selector 256 which is coupled to a reference store 255 in which is stored a look-up table of interpolating factors. These factors conform to points on a sinusoidal weighting curve representative of the distribution of radiation intensity across the exploring beams. The unit 134 is the display and/or print-out and/or record unit, such as has been referred to earlier in relation to FIG. 3.

Figure 11:
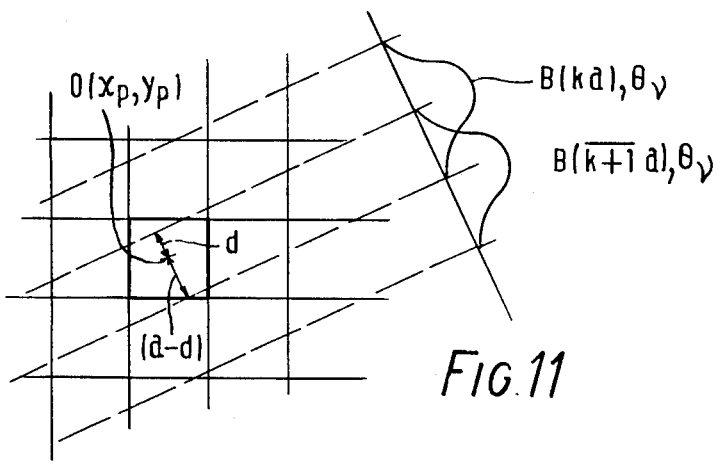
FIG. 11 is a diagram explanatory of the operation of FIG. 10.

For the purpose of filling the store 254 with the required data, the selector 256 selects addresses of store 254 in sequence and having chosen any one address it relates it in turn to addresses of the intermediate store sections $253_1, 253_2, 253_3, 253_4, \ldots$, by reference to the beam path data store 257. The addresses of the store 254 denote the co-ordinates of the mid-points of the mesh elements of the Cartesian meshwork upon which the final image reconstruction, as indicated earlier, is based. A small part of the Cartesian meshwork is depicted in FIG. 11, and in that mesh the mid-point 0 of a representative mesh is denoted by the co-ordinates $x_p, y_q$. The addresses of the store 253 denote the center lines of the beams of parallel sets as will have been understood from the description relating to FIGS. 8 and 9, one store section being concerned with the beams of one respective parallel set. For example, two beams B(ka), and $B(\overline{k+1}a)$ of the parallel set at angle $\theta_v$ are represented in FIG. 11, and there are addresses corresponding to the two beams in the store 253. In general, none of the center lines of the beams of any parallel set will pass through the mid-point of any particular mesh element corresponding to an address in the store 254 that has been selected by address selector 256, though it may pass very closely to such a point, or less so as the case may be. For example, in FIG. 11 the center lines of B($ka$), and B($\overline{k+1}a$) are distanced $d$ and $(a-d)$ respectively from the point 0. The beam path data store 257 has stored in it for each address of the store 254 an indication of the two beams in each set, the center lines of which lie immediately on each side of the mid-point of the address in question. These two beams may be said to bracket the mid-point. There is also stored an indication of the distances of the respective beam center lines to the mid-point address. It will be understood that this information is determined by the construction of the apparatus and can therefore be stored permanently in the computer. When the address selector 256 selects any particular address in the output matrix store 254, it derives at the same time from the beam path data store 257 the indication of the two beams in every set which bracket the selected address in the store 254. For example in the case of the address $x_p, y_q$ in store 254, the beam path data store contains information that the two bracketing beams of the set at the angle $\theta_v$, are beams B$ka$ and B($\overline{k+1}a$) at distances $d$ and $(a-d)$. The address selector 256 then selects the two appropriate addresses in each section of store 253 and causes the magnitudes in each such pair of addresses to be passed to the interpolation unit 255. The information about the distances of the beam center lines from the selected address in the store 254 is applied at the same time to the interpolator 255. The two magnitudes so selected from each section of store 253 are each sinusoidally weighted by appropriate sinusoidal weighting factors selected in the interpolator 255 in response to the distance indications received from 257. The weightings have the effect in every instance of assessing the constribution made by each of the two selected magnitudes to the mesh element in question. The selected data from each section of store 253 is transferred after weighting by the interpolator 255 in the appropriate address $x_p, y_q$ in the store 254 and is summed therein. The same process is repeated for every address in the store 254. The interpolator 255 contains a look up table containing for example 20 weighting factots equally spread with respect to distance from beam center line and conforming to the sinusoidal interpolation function, the weighting factors used in the interpolation being derived from this table. All the components shown in FIG. 9 are realised in practise by a programmed digital computer. If image reconstruction less accurate than that obtainable from the arrangement of FIG. 10 would be acceptable, the interpolator 255 may be omitted.

To illustrate this, consider the magnitudes stores at the addresses $A_0, A_1, A_2, A_3, A_4, \ldots A_\omega$ of any section of the intermediate store 253 in the way that has been described, this section representing a typical section of store 253. The address $A_0$ is considered to correspond to the first beam of the parallel set envisaged (the beam intercepted by the lead 23 not being included), and the magnitude finally stored at address $A_0$ is transferred to all those addresses of the meshwork store 254 corresponding to meshes of the Cartesian meshwork intercepted by the center line of this beam. Again address $A_1$ is considered to correspond to the second beam of the parallel set, and the magnitude stored at address $A_1$ is transferred to all those addresses of store 254 corresponding to meshes intercepted by the center line of the second beam. This transfer procedure continues until all the magnitudes stored at the addresses $A_0, A_1, A_2, A_3, A_4, \ldots A_\omega$ are used up. The procedure is followed out also for all other sections of the store 253 to yield by addition in store 254 an appropriate final image reconstruction. If desired the transfer to the store 254 can be restricted to a limited number of addresses of store 254 corresponding to locations only within a restricted area of the cross-section under examination.

The present invention is primarily concerned with the method and apparatus for achieving image reconstruction in a way which is correctly related to the physical parameters of the system for deriving the data relating to the logarithmic absorption suffered by an exploring beam traversing many sets of parallel beam paths. The method and apparatus correctly takes account of the parameters of the sets of beams and insofar as approximations are made, they are justifiable in terms of the system. The apparatus shown in FIG. 1 and 2 for deriving beam absorption data is however given only by way of example and the method and apparatus for image reconstruction in accordance with the invention is applicable to any system for deriving absorption data from many sets of substantially parallel beam paths. As indicated the apparatus used for the image reconstruction which is illustrated is realised to a large extent by a suitable programmed digital computer, which apart from some of the components shown in FIG. 2, and the components shown in FIG. 8, may be a general purpose computer. However the computer may to a greater or less degree be constituted by special integrated and printed circuits and permanent stores. Moreover, the apparatus produced by the L-factor data processor 252 may be assigned directly to the output matrix store, without intermediate storage in 253. In this case, two dimensional address would be carried out in the store 255.

Where reference is made herein and in the claims to producing or constructing a representation of the variation of absorption of a planar slice it will be understood that the quantity represented need not be the absorption explicitly, and the representation may be of some function of absorption (such as transmission to the radiation) or may be of differences of absorption.

What I claim is:

1. Apparatus for examining a substantially planar section of a body by means of penetrating radiation, especially X-or $\gamma$ -radiation, comprising a source of the radiation, a detecting arrangement for detecting radiation emergency from the section along at least one beam, scanning means arranged to cause said detecting arrangement to provide data signals representing the transmission or absorption of radiation passing through the section along sets of beams orientated at different angles in said section, and circuit means for constructing a representation of the transmission or absorption of said radiation at different locations in said section, the circuit means including storage elements corresponding to said locations and means for accumulating, in each storage element, signals derived from the data signals and relating to beams passing through or adjacent the corresponding locations, the improvement comprising; a signal modifying device having input and output connections and a recirculatory signal path linking said input and output connections, means for applying the data signals relating to a set of beams, in regular time sequence, to said input connection, a multiplying circuit for multiplying, by a factor less than unity, signals traversing said signal path and for applying the product to said input connection and means for combining said product with the next signal in said sequence so that, as the data signals relating to a set of beams are applied sequentially to said input connection, output signals appear in succession at said output connection, each corresponding to a respective one of said data signals and some at least of said output signals including contributions from other data signals of the same set each said contribution comprising a data signal multiplied by a respective one of a series of progressively diminishing factors, related to the spacing between the beam to which said respective one of said data signals relates and the beams to which said other data signals relate, means being provided for distributing the output signals so derived to the storage elements corresponding to the locations in said section intersected by the beam to which said respective one of said data signals relates.

2. Apparatus according to claim 1 having means for applying each set of signals twice to the signal modifying device, the order of the sequence being reversed for the second application as compared with the first so that two sets of summation signals are applied to said storage elements, allowance being made for duplication of signals distributed to some of said storage elements.

3. Apparatus according to claim 1 having means for applying a final correction signal to each summation signal to correct for the fact that signals passing directly from said input connection to said output connection should be of different sign from recirculated signals.

4. Apparatus according to claim 1 including at least one further signal modifying device, similar to the first mentioned signal modifying device except that the said multiplying factor is different, means for applying said data signals in parallel to each of said devices and means for combining the output signals appearing contemporaneously at the output connections of said devices.

5. Medical radiographic apparatus comprising means defining a patient position, a source of X-radiation, arranged to project said radiation through a substantially planar region of said patient position, scanning means for scanning said source relative to said patient position so as to project said radiation through said position along a plurality of sets of beams, the beams of a set being distributed across said region and each set being orientated at a respective angle to the patient position in said region, detector means for detecting the radiation emergent from said position along each of said paths and for producing data signals indicative of the amount of radiation projected through said position along each of said paths, means for processing said data signals to provide a representation of the absorption coefficient, with respect to said radiation, at each of a plurality of locations distributed over said region; said processing means including at least one circuit having an input terminal and an output terminal, means for applying the data signals relating to a set of beams in sequence and at a predetermined rate to said input terminal, said at least one circuit including a delay line, having a delay corresponding to said rate, an adding circuit, connected to said input terminal, through which said data signals pass before application to the input of said delay line, and a multiplying circuit, connected in the path of data signals which have traversed said adding circuit for multiplying signals applied thereto by a factor less than unity, the components of said at least one circuit being interconnected so that a signal applied to said input terminal traverses said adding circuit and returns, duly multiplied, to said adding circuit in time to be combined therein with the next data signal in the sequence; the output terminal being connected to the output of the adding circuit and thus receiving, in sequence, as the data signals of a set are applied to said input terminal, output signals, each comprising one of said data signals combined with different proportions of any data signals of the same set previously applied to said circuit.

6. Apparatus according to claim 5 including a further multiplying circuit connected to said output terminal for multiplying said output signals by a substantially constant factor.

7. Apparatus for examining a substantially planar region of a body by means of penetrating radiation, such as X- radiation, including a scanning apparatus for providing data signals indicative of the amount of said radiation transmitted through said region along respective, substantially co-planar beam paths; a signal modifying device including a combining circuit and a recirculatory signal path having its junction at said combining circuit; means for applying said data signals in a predetermined sequence to said combining circuit; said signal modifying device also including a multiplying circuit for multiplying, by a factor less than unity, signals traversing said recirculatory signal path and means for applying the product of said multiplication to said combining circuit in time to be combined with the next data signal in said sequence; means being provided for successively sampling the signals in said recirculatory signal path to provide output signals corresponding to said data signals, some at least of said output signals including a contribution from at least one other data signal, the contribution comprising said at least one other data signal multiplied at least once by said factor.

8. A method of examining a substantially planar region of a body by means of penetrating radiation, such as X- radiation, including the steps of:
 a. deriving data signals indicative of the amount of said radiation transmitted through said region along respective, substantially co-planar beam paths,
 b. applying said data signals in a predetermined sequence to the input of a recirculatory signal path,
 c. multiplying, by a factor less than unity, signals traversing said recirculatory signal path, to produce product signals,
 d. combining each product signal as it returns to the input of said recirculatory signal path, with the next data signal in said sequence applied thereto to produce combination signals,
 e. deriving from said recirculatory signal path output signals indicative of successively produced combination signals, and
 f. utilising said output signals to produce a representation of the variation in absorption of said radiation over said region.

* * * * *